(12) United States Patent
Gupta et al.

(10) Patent No.: US 9,975,913 B2
(45) Date of Patent: May 22, 2018

(54) METHOD FOR IN-GEL VISUAL DETECTION OF BIOANALYTES

(71) Applicant: Council of Scientific & Industrial Research, New Delhi (IN)

(72) Inventors: Sayam Sen Gupta, Maharashtra (IN); Sushma Kumari, Maharashtra (IN); Chakadola Panda, Maharashtra (IN)

(73) Assignee: Council of Scientific & Industrial Research, New Delhi (IN)

(*) Notice: Subject to any disclaimer, the term of this patent is extended or adjusted under 35 U.S.C. 154(b) by 0 days. days.

(21) Appl. No.: 15/202,286

(22) Filed: Jul. 5, 2016

(65) Prior Publication Data

US 2017/0016854 A1 Jan. 19, 2017

(30) Foreign Application Priority Data

Jul. 13, 2015 (IN) .......................... 2106/DEL/2015

(51) Int. Cl.
| | | |
|---|---|---|
| *C07F 15/00* | (2006.01) | |
| *C07F 15/02* | (2006.01) | |
| *G01N 33/68* | (2006.01) | |
| *G01N 27/447* | (2006.01) | |

(52) U.S. Cl.
CPC ....... *C07F 15/025* (2013.01); *G01N 33/6803* (2013.01); *G01N 27/44747* (2013.01)

(58) Field of Classification Search
CPC .................................................... C07F 15/025

USPC .......................................................... 436/63
See application file for complete search history.

(56) References Cited

PUBLICATIONS

Sushma Kumari, Basab B. Dhar, Chakadola Panda, Abhishek Meena, and Sayam Sen Gupta "Fe-TAML Encapsulated Inside Mesoporous Silica Nanoparticles as Peroxidase Mimic: Femtomolar Protein Detection" ACS Appl. Mater. Interfaces 2014, 6, 13866-13873 (Year: 2014).*

Jaime Renart, Jakob Reiser, and George R. Stark "Transfer of proteins from gels to diazobenzyloxymethyl-paper and detection with antisera: A method for studying antibody specificity and antigen structure" Proc. Natl. Acad. Sci. USA vol. 76, No. 7, pp. 3116-3120, Jul. 1979 Biochemistry (Year: 1979).*

Chakadola Panda, Munmun Ghosh, Tamas Panda, Rahul Banerjee and Sayam Sen Gupta "Fe(III) complex of biuret-amide based macrocyclic ligand as peroxidase enzyme mimic" Chem. Commun., 2011, 47, 8016-8018 (Year: 2011).*

* cited by examiner

*Primary Examiner* — Christine T Mui
*Assistant Examiner* — Emily R. Berkeley
(74) *Attorney, Agent, or Firm* — Knobbe, Martens, Olson & Bear LLP

(57) ABSTRACT

The present invention relates to a method for in-gel visual detection and quantitative detection of proteins in activity based protein profiling (ABPP) using horseradish peroxidase mimic $Fe^{III}$-TAML complex of ligand as a catalytic probe. The invention further relates to kit comprising compounds of formula (I) and method for the detection of bioanalytes using kit comprising compounds of formula (I).

16 Claims, 8 Drawing Sheets

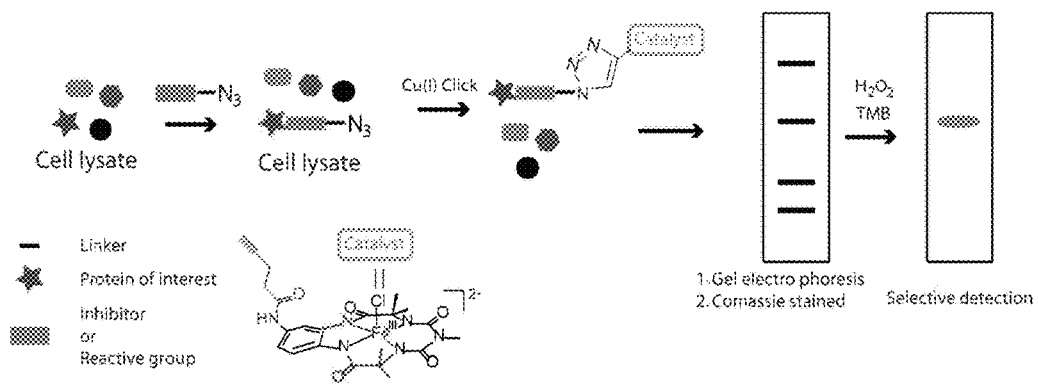
Figure: 1

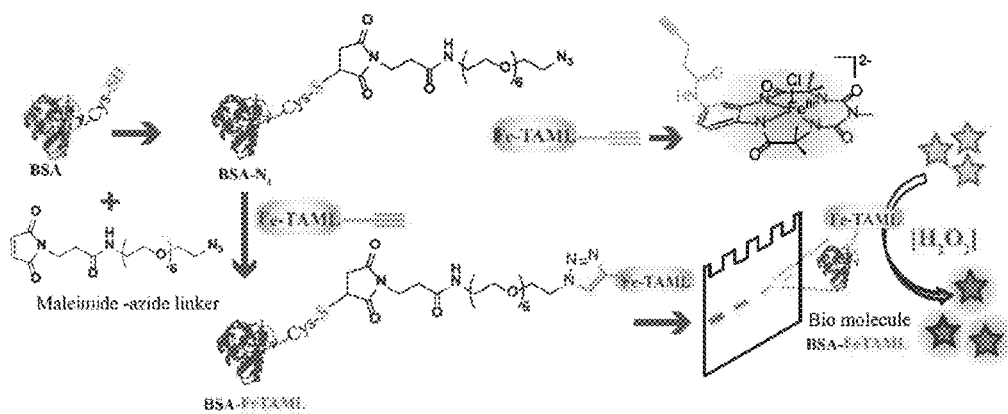
Figure: 2

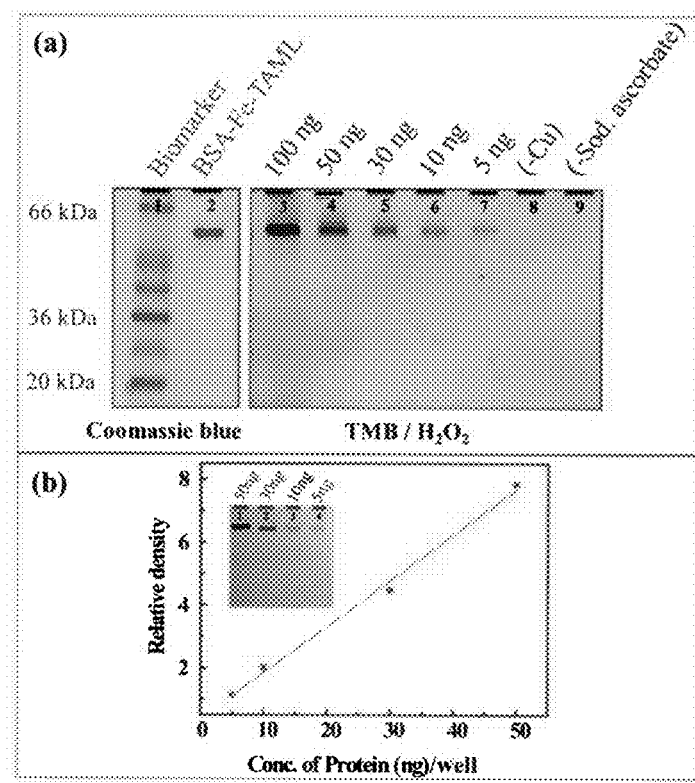
Figure: 3

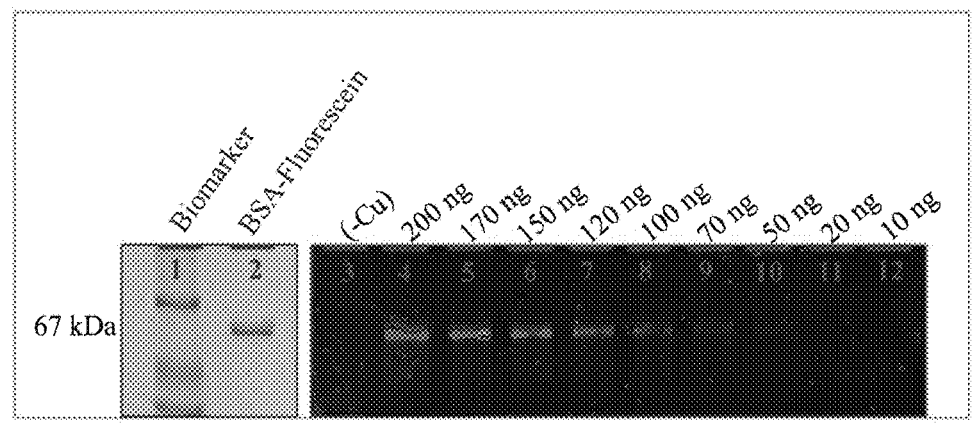
Figure: 4

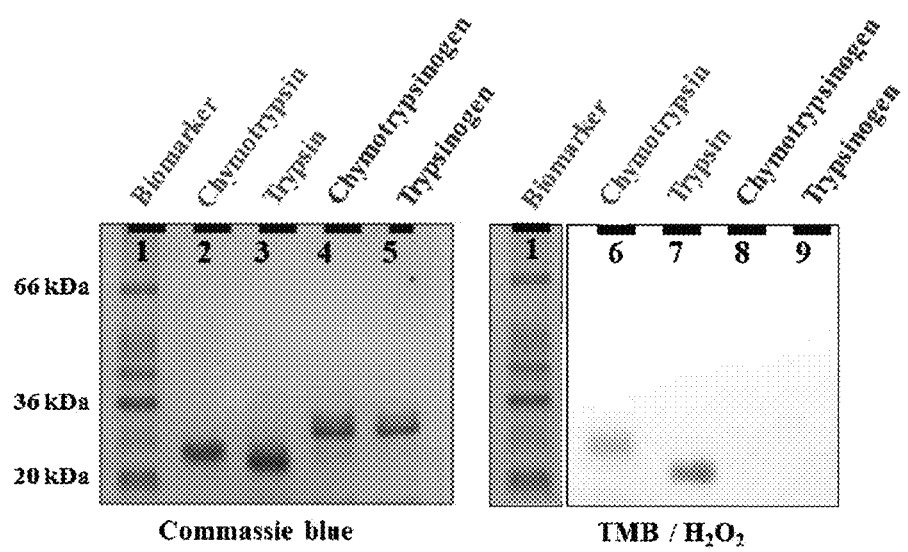
Figure: 5

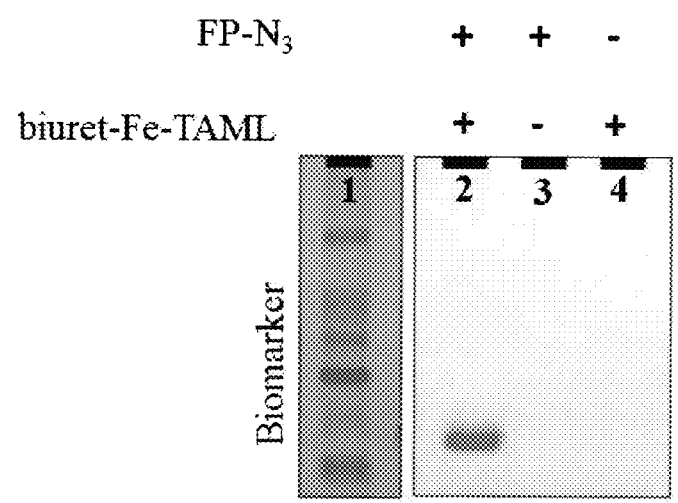
Figure: 6

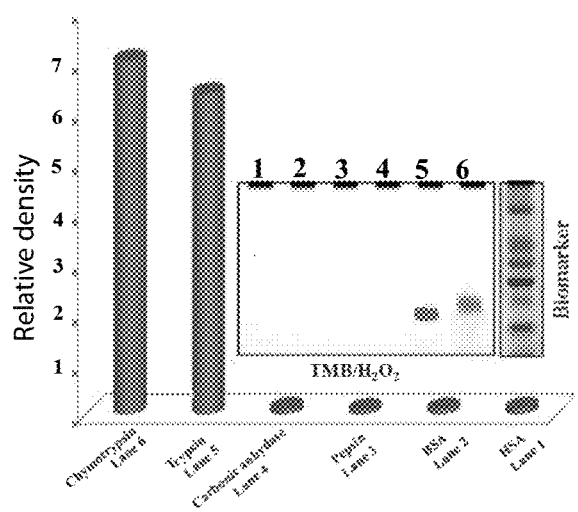
Figure: 7

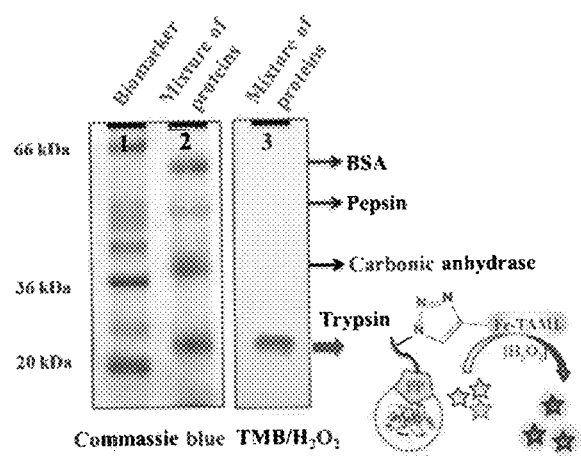
Figure: 8

METHOD FOR IN-GEL VISUAL DETECTION OF BIOANALYTES

CROSS-REFERENCE TO RELATED APPLICATIONS

This application claims the benefit of priority to Indian Patent Application No. 2106/DEL/2015, filed on Jul. 13, 2015, the disclosure of which is hereby expressly incorporated by reference in its entirety.

FIELD OF THE INVENTION

The present invention relates to the field of analytical proteomics. More specifically, the present invention relates to a method for in-gel visual detection and quantitative detection of proteins in proteomic applications such as activity based protein profiling (ABPP) using horseradish peroxidase mimic $Fe^{III}$-TAML complex of ligand as a catalytic probe. The invention further relates to a kit comprising compounds of formula (I) and methods for the detection of bioanalytes using the kits comprising compounds of formula (I).

BACKGROUND AND PRIOR ART

Proteins play a very vital role in humans and perform different body functions which are vital to life. Their presence and/or absence have been correlated with several diseases. Therefore, detection and quantification of each protein is very important in medicine including in early detection of diseases. Typically assays like ELISA or western blot assays are used for such detection. The conceptual novelty of both these assays which allow detection of very low quantities of proteins is in the use of catalytic signal amplification: a single analyte molecule recruits an enzyme able to generate a multitude of reporter molecules, which is ultimately determined by the turn-over number of the enzyme. One enzyme which is very routinely used for signal amplification is horseradish peroxidise (HRP), which in the presence of $H_2O_2$ converts a non-chemiluminiscent molecule into a chemiluminiscent molecule with several thousand turnovers, thus decreasing the detection limits by several folds. Both these assays have severe limitations including (i) storage and handling of antibody/enzymes (ii) and prohibitive cost of antibody conjugated HRP, horse radish peroxidase (HRP) and (iii) long duration of the assays. In spite of these limitations they are being used extensively in analytical proteomics.

Detection of low concentration of proteins and other bio-markers is extremely important for early diagnosis of lethal diseases. Extensive efforts are being made by research groups to develop suitable chemical and biological probes that permit detection of a particular protein at low concentration in a complex proteome by the naked eye. High throughput detection of biomarkers can therefore be achieved without the use of much sophisticated instrumentation (which is therefore easy and inexpensive). Typical probes consist of two domains: chemical or biological domain, which specifically binds to the protein of interest; and a reporter molecule attached to it, which produces an output signal (e.g. fluorophore which gives a fluorescence output). For direct assays, in which fluorescent dyes such as fluorescein or rhodamine are commonly used as reporter molecules, the strength of the output signal is determined by the magnitude of the binding constant between the probe and the protein, together with the extinction coefficient and fluorescence quantum yield of the reporter molecule. Typically, therefore, detection limits are increased by improving the fluorescence output of the reporter molecule.

As an alternative, ABPP has emerged as a key technology in the evolution of functional proteomics. ABPP relies on the design of active-site directed covalent probes to investigate specific families of enzymes in complex proteomes. The fundamental building blocks of ABPP are small-molecule probes that covalently label the active site of a given enzyme or enzymes. These inhibitor probes which get covalently bound to the enzyme of interest are attached to a reporter tag to facilitate target characterization. Examples of reporter tags include fluorophores, biotin, and latent analytical handles such as alkynes or azides, which can be modified by click chemistry methods to visualize protein targets post-labeling by gel electrophoresis as has been shown by Cravatt et. al in Chemistry & Biology, April 2004, volume 11, issue 4, pp 535-546. Typically, fluorescent probes like rhodamine is used as the reporter tag and this limits the detection limit for the enzyme of interest. Further expensive analytical tools such as the gel doc system are required for visualization.

Article titled "In-gel detection of biotin-protein conjugates with a green fluorescent streptavidin probe" by AE Sorenson et al. published in *Anal. Methods*, 2015, 7, pp 2087-2092 reports a simple and reliable electrophoretic method to determine the relative extent of biotinylation of macromolecules. The method relies on complex formation between a biotinylated macromolecule and a streptavidin probe resulting in an electrophoretic mobility shift of the complex detectable by SDS-PAGE.

Thus there is an unmet need in the art since detection of very low concentration of proteins using fluorescent dye labelling requires very expensive fluorescence gel scanning systems.

Another drawback of state of art reagents available till date is that very few afford the biochemist the freedom to conduct a simple visual detection of proteins across a large range of the analyte concentration with a low, preferably extremely low limit of detection.

Accordingly, to overcome the above listed drawbacks of the various agents available for protein detection and quantification, the present invention provides a small molecule peroxidase mimic biuret-Fe-TAML i.e. horseradish peroxidase mimic $Fe^{III}$-TAML complex of ligand as a catalytic probe for in-gel visual detection and quantitative detection of proteins in activity based protein profiling.

SUMMARY OF THE INVENTION

The present invention provides an efficient, one step detection method for in-gel visual detection and quantitative detection of bioanalytes by treating the same with a compound of formula (I). The methods described herein, desirably, eliminate the need for expensive gel doc visualization systems and provide low limits of detection.

Aspects of the invention concern the compounds of formula (I), which are used for chemoselective labeling of bioanalytes and the subsequent visual detection of the conjugate in a polyacrylamide gel by catalytic signal amplification.

More alternatives concern methods for detection of bioanalytes in a gel using the compounds of formula (I).

Still more alternatives concern kits comprising the compounds of formula (I).

Yet more alternatives concern methods for the detection of bioanalytes, which utilize a kit comprising the compounds of formula (I).

Accordingly, the present invention provides compounds of formula (I)

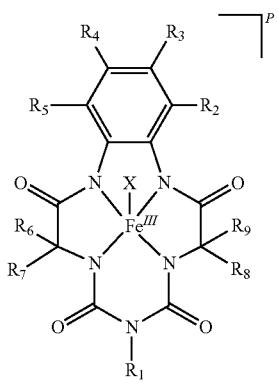

Formula (I)

Wherein, X is a mono ionic ligand, selected from chloro, bromo and iodo or neutral ligands such as $H_2O$ and $R_1$, $R_2$, $R_3$, $R_4$, $R_5$, $R_6$, $R_7$, $R_8$ and $R_9$ are same or different selected from the group consisting of hydrogen, alkyl, alkenyl, alkynyl, aryl, alkoxy, phenoxy, halogen, halogenated alkyl, halogenated alkenyl, halogenated alkynyl, a substituted or unsubstituted cycloalkyl ring, substituted or unsubstituted cycloalkenyl ring, a substituted or unsubstituted saturated heterocyclic ring, a substituted or unsubstituted unsaturated heterocyclic ring, carboxylic acid, carboxylic acid ester, carboxylic acid halides, amines, nitro, and nitrile and, wherein P represents a cation selected from Li, Na, K, $Et_4N$, or $Ph_4P$.

In another aspect, the present invention provides a method for the detection of analytes by using compound for formula (I).

In still another aspect, the present invention is to provide a kit comprising compound of formula (I).

In yet another aspect, the present invention is to provide a method for the detection of bio analytes using kit which comprises compounds of formula (I).

BRIEF DESCRIPTION OF THE DRAWINGS

The disclosure may be more fully understood by reading the following detailed description of the embodiment, with reference made to the accompanying drawings as follows:

FIG. 1: depicts concept of signal amplification by biuret-Fe-TAML in ABPP, FIG. 1 is a schematic representation of ABPP using catalytic signal amplification for in-gel visual detection of proteins. Different shapes represent different proteins FIG. 2: depicts synthesis of $BSA-N_3$ followed by CuAAC using alkyne-biuret-Fe-TAML. Schematic representation for the analysis of BSA-Fe-TAML conjugate using SDS-PAGE. After gel electrophoresis, treatment with $TMB/H_2O_2$ leads to formation of oxidized TMB; thus appearing as a blue color band at the expected location of the BSA in the gel. The catalytic formation of oxidized TMB leads to signal amplification and in turn lowers the limit of detection.

FIG. 3: depicts SDS-PAGE of the BSA labelled with alkyne-biuret-Fe-TAML (a) Lane 1-2: Protein bands by Coomassie staining; Lane 3-9: Protein bands after treatment with 0.05 mM TMB/20 mM $H_2O_2$. Lane 1: biomarker; Lane 2: BSA-Fe-TAML; Lane 3-9: BSA-Fe-TAML with varying amounts of protein (100-5 ng) loaded in each well. (b) Relative quantification of protein from the band intensity using Image J for Lanes 1-4.

FIG. 4: depicts visualization of the reaction mixture after CuAAC with fluorescein-alkyne and $BSA-N_3$ by Gel Doc. Lane 1and 2: Coomassie staining of biomarker and fluorescein conjugated $BSA-N_3$ respectively; Lane 3-12: Fluorescence imaging of protein bands using Gel Doc. Lane 1: biomarker; Lane 2: BSA-Fluorescein (200 ng); Lane 3-12: BSA-Fluorescein with varying amounts of protein (200-10 ng) loaded in each well.

FIG. 5: depicts SDS-PAGE of the serine proteases labelled with FP-Fe-TAML. Labelled proteins were quenched with SDS loading buffer and analysed by SDS-PAGE. Lanes 2-5 (10 μg/lane): Coomassie stained; Lanes 6-9 (100 ng/lane): Treatment with 0.05 mM TMB/20 mM $H_2O_2$. Lane 1: Biomarker; Lane 2, 6: Chymotrypsin; Lane 3, 7: Trypsin; Lane 4, 8: Chymotrypsinogen; Lane 5, 9: Trypsinogen.

FIG. 6: depicts SDS-PAGE analysis to confirm the covalent attachment of $FP-N_3$ labelled trypsin with alkyne-biuret-Fe-TAML using CuAAC. The gel was treated 0.05 mM TMB/20 mM $H_2O_2$ for visualisation of the protein bands. Lane 1: biomarker with Coomassie staining; Lane 2: trypsin labelled with FP-Fe-TAML; Lane 3: trypsin conjugation reaction in absence of biuret-Fe-TAML; Lane 4: trypsin conjugation reaction in absence of $FP-N_3$ (auto digested trypsin).

FIG. 7: depicts selectivity of $FP-N_3$/alkyne-biuret-Fe-TAML towards labelling of serine proteases over Carbonic Anhydrase, Pepsin, BSA and HSA. Relative intensity of the bands observed after treatment with $TMB/H_2O_2$ for Trypsin and Chymotrypsin (lane 5 and 6) was much higher than that of the other proteins (Lanes 1-4). The band intensity was analysed using Image J. Inset: SDS-PAGE gel of Trypsin, Chymotrypsin, Carbonic Anhydrase, Pepsin, BSA and HSA after treatment with $FP-N_3$/alkyne-biuret-Fe-TAML and subsequently probed by $TMB/H_2O_2$. Lane 1-4: HSA, BSA, Pepsin, Carbonic Anhydrase (100 ng/well). Lane 5 and 6: Trypsin and chymotrypsin (100 ng/well).

FIG. 8: depicts selectivity of $FP-N_3$/alkyne-biuret-Fe-TAML towards labelling of Trypsin from a mixture of proteins. Lane 1: Biomarker. Lane 2: Mixture of proteins (BSA, Pepsin, Carbonic anhydrase and Trypsin) (10 μg/well) that were Coomassie stained. Lane 3: Mixture of proteins (100 ng/well) probed with 0.05 mM TMB/20 mM $H_2O_2$.

Abbreviations
TMB-3,3',5,5'-Tetramethylbenzidine.
THPTA-Tris(3-hydroxypropyltriazolylmethyl)amine
SDS-Sodiumdodecylsulphate.
biuret-Fe-TAML-Fe (III) complex of a biuret amide based tetraamide macrocyclic ligand.

DETAILED DESCRIPTION OF THE INVENTION

The invention will now be described in detail in connection with certain preferred and optional embodiments, so that various aspects thereof may be more fully understood and appreciated.

The present invention provides compounds of formula (I) for chemoselective labeling of proteins and the subsequent visual detection of the conjugate in a polyacrylamide gel by catalytic signal amplification in activity based protein profiling (ABPP).

In an embodiment, the present invention provides compound of formula (I) for detection of bioanalytes;

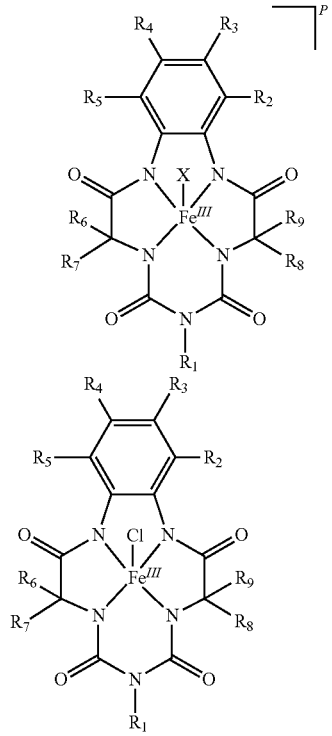

Formula (I)

Wherein, X is is a mono ionic ligand, selected from chloro, bromo and iodo or neutral ligands such as $OH_2$ and $R_1$, $R_2$, $R_3$, $R_4$, $R_5$, $R_6$, $R_7$, $R_8$ and $R_9$ are the same or are different and are selected from the group consisting of hydrogen, alkyl, alkenyl, alkynyl, aryl, alkoxy, phenoxy, halogen, halogenated alkyl, halogenated alkenyl, halogenated alkynyl, a substituted or unsubstituted cycloalkyl ring, substituted or unsubstituted cycloalkenyl ring, a substituted or unsubstituted saturated heterocyclic ring, a substituted or unsubstituted unsaturated heterocyclic ring, carboxylic acid, carboxylic acid ester, carboxylic acid halides, amines, nitro, and nitrile and wherein, P represents a cation selected from Li, Na, K, $Et_4N$, or $Ph_4P$.

In a preferred embodiment, the compound of formula (I) is biuret-Fe-TAML complex.

With the view to increase limit of detection for protein detection in activity based protein profiling, the present invention provides a small molecule peroxidase mimic biuret-Fe-TAML e.g., horseradish peroxidase mimic $Fe^{III}$-TAML complex of ligand, which would amplify the signal to lower the detection limit.

The compound of formula (I) of the present invention, which is a peroxidase mimic, has an advantage over the conventional fluorescent e.g., said compound of formula (I) amplify the signal to lower the detection limit and allow for in gel visual detection.

Accordingly, in another embodiment, the invention provides a method for in-gel visual detection and quantitative detection of bioanalyte comprising a step of treating the bioanalyte with a compound of formula (I) as a catalytic probe.

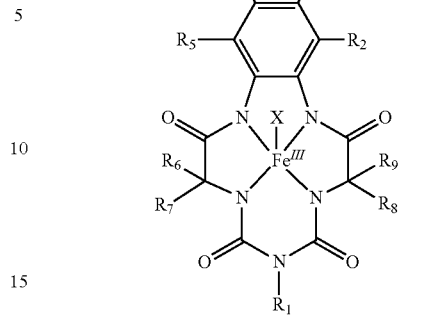

Formula (I)

wherein, X is is a mono ionic ligand, selected from chloro, bromo and iodo or neutral ligands such as $OH_2$ and $R_1$, $R_2$, $R_3$, $R_4$, $R_5$, $R_6$, $R_7$, $R_8$ and $R_9$ are the same or are different and are selected from the group consisting of hydrogen, alkyl, alkenyl, alkynyl, aryl, alkoxy, phenoxy, halogen, halogenated alkyl, halogenated alkenyl, halogenated alkynyl, a substituted or unsubstituted cycloalkyl ring, substituted or unsubstituted cycloalkenyl ring, a substituted or unsubstituted saturated heterocyclic ring, a substituted or unsubstituted unsaturated heterocyclic ring, carboxylic acid, carboxylic acid ester, carboxylic acid halides, amines, nitro, and nitrile, and wherein, P represents a cation selected from Li, Na, K, $Et_4N$ or $Ph_4P$.

In yet another embodiment the compound of formula I is horseradish peroxidase mimic $Fe^{III}$-TAML complex of ligand.

In an embodiment the method of the present invention comprising:
  a) treating the mixture of bio analyte with an inhibitor probe that has an organoazide handle to obtain azide labelled bio analyte;
  b) subjecting the mixture of step (a) to click reaction with an alkyne-tagged biuret-Fe-TAML;
  c) running the mixture of step (b) on a polyacrylamide gel followed by probing with $H_2O_2$ and 3,3',5,5'-Tetramethylbenzidine (or related probes) and
  d) observing blue colored band for the bioanalyte.

In another embodiment the organoazide is maleimide-azide.

In one embodiment the bio analyte is selected from proteins, enzymes, antibodies, or nucleic acids and the like.

In another embodiment the bio analyte is a protein, preferably Bovine Serum Albumin (BSA).

In an aspect of the present invention the method is conducted by catalytic signal amplification in activity based protein profiling (ABPP).

In one of the embodiment, the present invention provides a method of lowering the detection limit for an enzyme (bioanalyte) of interest in a mixture of enzymes, wherein said method comprises:
  a) treating the mixture of enzymes with an inhibitor probe that has an organoazide handle to obtain azide labelled enzyme;
  b) subjecting the enzyme mixture of step (a) to click reaction with an alkyne-tagged biuret-Fe-TAML;
  c) running the mixture of step (b) on a polyacrylamide gel followed by probing with $H_2O_2$ and TMB (or related probes) and d) observing blue colored band for the enzyme to which the biuret-Fe-TAML has been covalently attached.

In another embodiment the organoazide is fluorophosphonate-azide (FP-$N_3$). Since biuret-Fe-TAML is a catalyst and can catalyze the production of several colored molecules, the detection limit of the enzyme of interest would be significantly lowered. It would also allow visual detection unlike most methods which require expensive instrumentation to detect fluorescence.

In yet another embodiment, the present invention provides a kit for detection of bio-analytes, wherein said kit comprises:
at least an alkyne tagged compound of formula (I).

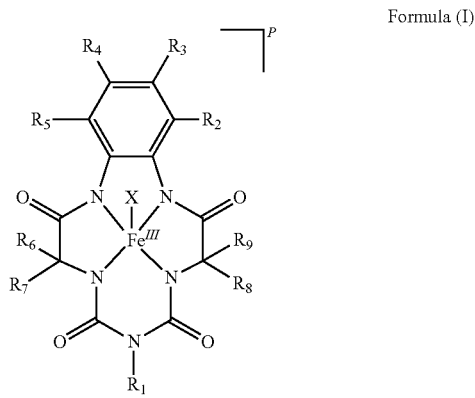

Formula (I)

wherein, X is is a mono ionic ligand, selected from chloro, bromo and iodo or neutral ligands such as $OH_2$ and $R_1$, $R_2$, $R_3$, $R_4$, $R_5$, $R_6$, $R_7$, $R_8$ and $R_9$ are the same or different and are selected from the group consisting of hydrogen, alkyl, alkenyl, alkynyl, aryl, alkoxy, phenoxy, halogen, halogenated alkyl, halogenated alkenyl, halogenated alkynyl, a substituted or unsubstituted cycloalkyl ring, substituted or unsubstituted cycloalkenyl ring, a substituted or unsubstituted saturated heterocyclic ring, a substituted or unsubstituted unsaturated heterocyclic ring, carboxylic acid, carboxylic acid ester, carboxylic acid halides, amines, nitro, and nitrile, with a proviso that at least one of R2 to R5 is alkyne, and wherein, P represents a cation selected from Li, Na, K, $Et_4N$ or $Ph_4P$;
a least a solution of Tris(3-hydroxypropyltriazolylmethyl)amine (THPTA); and
hydrogen peroxide $H_2O_2$;

In another embodiment, said bio-analyte is selected from the group consisting of azide labeled Bovine Serum Albumin(BSA-$N_3$) or serine proteases.

In yet another embodiment, the present invention provides a kit for visual detection of azide labeled Bovine Serum Albumin(BSA-$N_3$), wherein said kit comprises:
alkyne biuret-Fe-TAML (1.6 mg) of 803.5 mol wt (g/mol);
reconstituted in 0.1 mL of DI water and of 20 mM stock, THPTA (2 mg) of 434.5 mol wt (g/mol);
reconstituted in 0.1 mL of DI water and of 50 mM stock, $CuSO_4.5H_2O$ (5 mg) of 250 mol wt (g/mol);
reconstituted in 1 mL of DI water and of 20 mM stock, Aminoguanidine. HCl (11 mg) of 110.5 mol wt (g/mol);
reconstituted in 1 mL of DI water and of 100 mM stock, Sodium ascorbate (19.8 mg) of 198.1 mol wt (g/mol);
reconstituted in 1 mL of DI water and of 100 mM stock, 1X Loading buffer of 1X stock, TMB (12 mg) of 240.5 mol wt (g/mol); and
reconstituted in 1 mL of 0.1N HCl and of 50 mM stock, and 30 wt % $H_2O_2$ (commercial) of 34 mol wt (g/mol); and of 8M stock.

In one embodiment, the present invention provides a kit for in-gel visual detection of serine proteases comprising:
FP-$N_3$ (2 mg) of 414 mol wt (g/mol);
reconstituted in 1 mL of DMSO and of 4.8 mM stock, Trypsin (1 mg)/Chymotrypsin (1 mg) of 23300/25000 mol wt (g/mol);
reconstituted in 1 mL of 50 mM tris buffer (pH 8.0) and of ~42 mM stock;
Alkyne biuret-Fe-TAML (1.6 mg) of 803.5 mol wt (g/mol);
reconstituted in 0.1 mL of DI water and of 20 mM stock, THPTA (2 mg) of 434.5 mol wt (g/mol);
reconstituted in 0.1 mL of DI water and of 50 mM stock, $CuSO_4.5H_2O$ (5 mg) of 250 mol wt (g/mol);
reconstituted in 1 mL of DI water and of 20 mM stock, Aminoguanidine. HCl (11 mg) of 110.5 mol wt (g/mol);
reconstituted in 1 mL of DI water and of 100 mM stock, Sodium ascorbate (19.8 mg) of 198.1 mol wt (g/mol);
reconstituted in 1 mL of DI water and of 100 mM stock, 1X Loading buffer of stock 1X, TMB (12 mg) of 240.3 mol wt (g/mol); and
reconstituted in 1 mL of 0.1N HCl and of 50 mM stock, and 30 wt % $H_2O_2$ (commercial) of 8M.

In one embodiment, the present invention provides a compound of formula (I), for use in or in a method of visual detection of bio analytes,

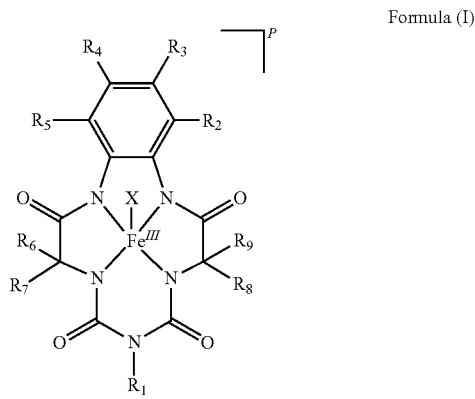

Formula (I)

wherein, X is is a mono ionic ligand, selected from chloro, bromo, or iodo or neutral ligands such as $OH_2$ and $R_1$, $R_2$, $R_3$, $R_4$, $R_5$, $R_6$, $R_7$, $R_8$ and $R_9$ are the same or are different and are selected form the group consisting of hydrogen, alkyl, alkenyl, alkynyl, aryl, alkoxy, phenoxy, halogen, halogenated alkyl, halogenated alkenyl, halogenated alkynyl, a substituted or unsubstituted cycloalkyl ring, substituted or unsubstituted cycloalkenyl ring, a substituted or unsubstituted saturated heterocyclic ring, a substituted or unsubstituted unsaturated heterocyclic ring, carboxylic acid, carboxylic acid ester, carboxylic acid halides, amines, nitro, and nitrile, and wherein, P represents a cation selected from Li, Na, K, $Et_4N$ or $Ph_4P$.

In another embodiment the compound is biuret-Fe-TAML complex.

In yet another embodiment, the compound of formula (I) is used to study the movement of materials into a cell. For example, in some embodiments, biuret-Fe-TAML is conjugated to polymers and/or nanoparticles and the catalytic activity of Fe-TAML is used to determine the amount of polymer and/or nanoparticle inside the cells.

Kits as mentioned above are tabulated below:

Kit-1:
Biuret-Fe-TAML as catalyst probe for in-gel visual detection of azide labeled Bovine Serum Albumin (BSA-N$_3$)

| Bottle no. | Reagent | Mol. wt (g/mol) | Reconstitution in | Stock |
|---|---|---|---|---|
| 1 | Alkyne biuret-Fe-TAML (1.6 mg) | 803.5 | 0.1 mL of DI water | 20 mM |
| 2 | THPTA (2 mg) | 434.5 | 0.1 mL of DI water | 50 mM |
| 3 | CuSO$_4$·5H$_2$O (5 mg) | 250 | 1 mL of DI water | 20 mM |
| 4 | Aminoguanidine·HCl (11 mg) | 110.5 | 1 mL of DI water | 100 mM |
| 5 | Sodium ascorbate (19.8 mg) | 198.1 | 1 mL of DI water | 100 mM |
| 6 | 1X Loading buffer | | | 1X |
| 6 | TMB (12 mg) | 240.3 | 1 mL of 0.1N HCL | 50 mM |
| 7 | 30 wt % H$_2$O$_2$ (commercial) | 34 | — | 8M |

Kit 2:
Biuret-Fe-TAML as catalyst probe for in-gel visual detection of serine proteases

| Bottle no. | Reagent | Mol. wt (g/mol) | Reconstitution in | Stock |
|---|---|---|---|---|
| 1 | FP—N$_3$ (2 mg) | 414 | 1 mL DMSO | 4.8 mM |
| 2 | Trypsin (1 mg)/ Chymotrypsin (1 mg) | 23300/ 25000 | 1 mL of 50 mM tris buffer (pH 8.0) | ~42 µM |
| 1 | Alkyne biuret-Fe-TAML (1.6 mg) | 803.5 | 0.1 mL of DI water | 20 mM |
| 2 | THPTA (2 mg) | 434.5 | 0.1 mL of DI water | 50 mM |
| 3 | CuSO$_4$·5H$_2$O (5 mg) | 250 | 1 mL of DI water | 20 mM |
| 4 | Aminoguanidine·HCl (11 mg) | 110.5 | 1 mL of DI water | 100 mM |
| 5 | Sodium ascorbate (19.8 mg) | 198.1 | 1 mL of DI water | 100 mM |
| 6 | 1X Loading buffer | | | 1X |
| 6 | TMB (12 mg) | 240.3 | 1 mL of 0.1N HCL | 50 mM |
| 7 | 30 wt % H$_2$O$_2$ (commercial) | 34 | — | 8M |

The following examples, which include preferred embodiments, will serve to illustrate the practice of this invention, it being understood that the particulars shown are by way of example and for purpose of illustrative discussion of preferred embodiments of the invention. Accordingly, it should not be construed of limiting the scope of the instant invention.

EXAMPLES

Example 1

(a) Synthesis of maleimide-azide linker (3)

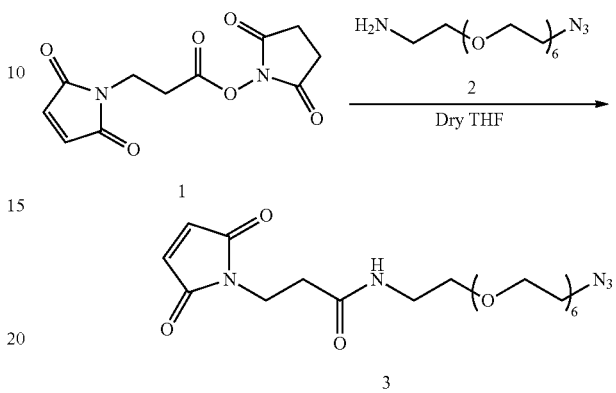

The maleimide-NHS linker (1) was prepared by the procedure reported in H. Y. Song, M. H. Ngai, Z. Y. Song, P. A. MacAry, J. Hobley, M. J. Lear, Org. Biomol. Chem. 2009, 7, 3400-3406. To a 0.75 ml solution of maleimide-NHS linker (7 mg; 26 mmol, 1eq) in dry THF was added a solution of azido-pegamine (2) (10 mg; 28.5 mmol, 1.1 eq) prepared in 0.75 ml of dry THF and stirred at room temperature for 1 hr. The reaction was monitored by TLC over time. After completion of the reaction, the product maleimide-azide (3) linker was taken out and kept at −20° C. for further protein conjugation reaction without any further purification. Considering 100% consumption of maleimide-NHS linker; concentration of maleimide-azide was assumed to be 17.3 mM. HR-MS showed m/z values 502 corresponding to the M-H+ species in the positive ion mode of the instrument.

(b) Labeling of the BSA with maleimide-azide (BSA-N$_3$)

To a solution of BSA (2 mg/mL; 1 mL) in 100 mM phosphate buffer pH 7.4 was added 40 µL of maleimide-azide with a molecular weight of 501 (0.6 mM, 20 eq) in 40 µL DMSO and the resulting solution was shaken overnight at 4° C. The reaction mixture was extensively purified by dialysis against 100 mM phosphate buffer pH 7.4 over 24 hour while changing the buffer after every four hours. The concentration of purified BSA-N$_3$ conjugate was confirmed by Bradford assay (~1.8 mg/mL) and was further used for protein-conjugation reactions.

(c) Conjugation of biuret-Fe-TAML on to BSA-N3 using azide-alkyne click reaction (CuAAC)

For the covalent attachment of biuret-Fe-TAML, CuAAC reaction was performed with BSA-N$_3$ (0.5 mg/mL) and alkyne biuret-Fe-TAML in the presence of CuSO$_4$, THPTA and sodium ascorbate for one hour at 4° C. The "click" reaction mixture described above was diluted with SDS-PAGE loading buffer, loaded onto the polyacrylamide gel (with concentrations ranging from 100 ng/well to 5 ng/well) and analysed by SDS-PAGE. The gel was subsequently treated with TMB and (20 mM) H$_2$O$_2$ (Kit 1; FIG. 3a), and within 60 sec a blue colored band was observed for all the concentrations at a position where BSA is expected (FIG. 3a, lanes 3-7). Upon co-localization of BSA-Fe-TAML with colorless substrate TMB and H$_2$O$_2$ in the polyacrylamide gel, oxidation of TMB occurs to form the corresponding one-electron oxidized product. This appears as a blue colored band in the gel. Although TMB and $H_2O_2$ is present in the rest of the gel, no color is observed as reaction between TMB and $H_2O_2$ is slow in absence of the catalyst. It accounts for a detection limit for 5 ng of protein per each well with a signal to noise ratio of 2. Control reaction w/o use of Cu or ascorbate shows no bands. To compare the detection limits with already published assays based on fluorescent probe, the experiment described above was performed with the exception of using fluorescein-alkyne (same quantity as that of the complex mentioned above) as the probe instead of alkyne biuret-Fe-TAML. The gel was analyzed in this case by Geldoc. A fluorescent band corresponding to BSA-$N_3$ was observed. However the detection limit was found to be 100 ng i.e. roughly 20 times higher than the catalyst probe biuret-Fe-TAML.

Example 2

Selective Labeling of Serine Hydrolases with FP-$N_3$ and Subsequent CuAAC for the Conjugation of Biuret-Fe-TAML To extend the assay to real sample analysis as achieved in ABPP, a fluorophosphonate-azide (FP-$N_3$) probe was designed which would have the ability to bind serine hydrolase family of enzymes and subsequently be "clicked" to alkyne-biuret-Fe-TAML. The strategy of azido-linked suicide inhibitor probes has been used by Cravatte et al. for profiling glycosyltransferases. An ABPP probe containing a fluorophosphonate war head, an oligoethyleneglycol linker and an alkyl-azide handle (FIG. 1). To test the efficacy of FP-$N_3$ towards serine hydrolases, FP-$N_3$ (40 µM) was incubated with equal amounts of two serine proteases (1 µM; trypsin and chymotrypsin) and their respective zymogens (trypsinogen and chymotrypsinogen) for 30 min. Proteins labelled with FP-$N_3$ were then incubated with biuret-Fe-TAML using CuAAC. The products of each reaction were diluted with SDS-PAGE loading buffer, analysed by SDS-PAGE (100 ng/well of protein) and probed with TMB/$H_2O_2$. FP-Fe-TAML strongly labelled both trypsin and chymotrypsin, but exhibited no reactivity with their corresponding proenzymes (FIG. 5) as was evident from the presence and absence of the blue colored band. Control experiments in which trypsin was first allowed to auto-digest for 15 min showed no bands upon addition of FP-$N_3$ followed by alkyne-biuret-Fe-TAML (FIG. 6). The selectivity of the FP-Fe-TAML probe towards serine proteases over other class of proteins such as human serum albumin (HSA), bovine serum albumin (BSA), pepsin and carbonic anhydrase was also evaluated. All the above mentioned proteins (0.5 mg/ml) were incubated with FP-$N_3$ for 30 min separately, followed by click reaction with alkyne-biuret-Fe-TAML. After completion of the reaction, analysis of the reaction mixture by SDS-PAGE/TMB/$H_2O_2$ showed that the blue-coloured bands were only obtained for the serine proteases, i.e trypsin and chymotrypsin, and not for other proteins (FIG. 7). This selectivity could be visually observed in the SDS-PAGE, and thus reveals the complete selectivity of FP-Fe-TAML towards the serine proteases.

Example 3

Selective Labelling of Serine Proteases in Presence of a Mixture of Proteins

To simulate a model proteome mixture, selectivity of the FP-$N_3$/alkyne-biuret-Fe-TAML probe towards serine protease was then evaluated in the presence of mixture of proteins (1 µM of each protein; FP-$N_3$ 100 µM). The protein mixture was incubated with FP-$N_3$ probe for 30 min, followed by CuAAC with alkyne-tagged biuret-Fe-TAML. Analysis by SDS-PAGE/TMB/$H_2O_2$ shows formation of a blue coloured band exactly where the Trypsin-FP-Fe-TAML conjugate was expected. No other bands were observed. The SDS-PAGE (FIG. 8) result demonstrates that using a combination of FP-$N_3$ and alkyne-biuret-Fe-TAML serine hydrolase enzymes can be effectively labelled and visually detected among a mixture of proteins.

Example 4

Mass Spectrometric Characterization of BSA-$N_3$ and BSA-Fe-TAML Conjugate

To determine the labelling site, the BSA-maleimide-$N_3$ conjugate was subjected to a tryptic digestion and subsequently analyzed by liquid chromatography/tandem mass Spectrometry. Forty-five unique peptides were identified, and 65.57% sequence coverage was obtained. The molecular weight of the peptide containing amino acids 21 to 41 [GLVLIAFSQYLQQCPFDEHVK] had an increase of 501 Da (corresponding to maleimide-$N_3$), thus showing that the modification occurred at Cys34 upon reaction with maleimide-$N_3$. Labelling of maleimide-$N_3$ to BSA was further confirmed by ESI-MS, which showed an increase of molecular mass 501 Da. For the subsequent covalent attachment of biuret-Fe-TAML, CuAAC reaction was performed with BSA-$N_3$ (0.5 mg/mL) and alkyne biuret-Fe-TAML in the presence of $CuSO_4$, THPTA and sodium ascorbate for one hour at 4° C. Successful labelling of BSA with biuret-Fe-TAML was confirmed by ESI-MS, showing an increase of mass by 1009 Da from the parent BSA. This increase corresponds to addition of both maleimide-$N_3$ linker and alkyne-biuret-Fe-TAML.

Example 5: In-Gel Visual Detection of BSA-$N_3$ Using Biuret-Fe-TAML as Catalyst Probe Kit 1

| Kit-1: Biuret-Fe-TAML as catalyst probe for in-gel visual detection of BSA-$N_3$ | | | | |
|---|---|---|---|---|
| Bottle no. | Reagent | Mol. wt (g/mol) | Reconstitution in | Stock |
| 1 | Alkyne biuret-Fe-TAML (1.6 mg) | 803.5 | 0.1 mL of DI water | 20 mM |
| 2 | THPTA (2 mg) | 434.5 | 0.1 mL of DI water | 50 mM |
| 3 | $CuSO_4 \cdot 5H_2O$ (5 mg) | 250 | 1 mL of DI water | 20 mM |
| 4 | Aminoguanidine•HCl (11 mg) | 110.5 | 1 mL of DI water | 100 mM |
| 5 | Sodium ascorbate (19.8 mg) | 198.1 | 1 mL of DI water | 100 mM |
| 6 | 1X Loading buffer | | | 1X |
| 6 | TMB (12 mg) | 240.3 | 1 mL of 0.1N HCL | 50 mM |
| 7 | 30 wt % $H_2O_2$ (commercial) | 34 | — | 8M |

Procedure for 200 µL Reaction Volume:

In a 1 mL eppendorf, 56 µL of BSA-$N_3$ (1.8 mg/ml) and 97 µL of 100 mM phosphate buffer pH 7.4 were added. To this solution were added 7.5 µL of alkyne-biuret-Fe-TAML (20 mM), 10 µL of premixed solution of $CuSO_4$ and THPTA ligand (stock solution containing 10 µL of 20 mM $CuSO_4$ and 20 µL of 50 mM THPTA ligand) and 10 µL of aminoguanidine hydrochloride (100 mM). The reaction mixture was well mixed with the help of a vortex and degassed by bubbling with $N_2$ gas (to remove $O_2$) followed by addition of 20 µL of freshly prepared sodium ascorbate (100 mM) solution under positive flow of $N_2$. After addition of sodium ascorbate, the reaction mixture was stirred for an additional hour. The reaction mixture was stirred for an hour at 4° C. For analysis by gel electrophoresis, 10 µL of the reaction mixture was added to 90 µL of 100 mM, pH 7.4 phosphate buffer and 100 µL of 1X SDS loading buffer. This solution was then analysed by SDS-PAGE.

The gel electrophoresis was carried out at a constant potential of 100 mV for typically 70 min (until the loading buffer band reaches the bottom of the gel). After completion of gel electrophoresis, the gel was taken out of the electrophoresis gel cassette, washed 4 to 5 times with DI water. A mixture of $H_2O_2$ (100 µL) and TMB (100 µL) in 5 mL of 50 mM PB at pH 7.4 was added with gentle agitation for 2 minutes. A nice blue coloured band appeared on the gel at a position where the BSA-Fe-TAML conjugate is expected based on the protein marker. The gel was then incubated with 50 mM PB pH 4.5 and the color of the blue band intensified due to the higher extinction co-efficient of the oxidized TMB at pH 4.5

Example 6: In-Gel Visual Detection of Serine Proteases Using Biuret-Fe-TAML as Catalyst Probe Kit 2

Kit-2:
Biuret-Fe-TAML as catalyst probe for in-gel visual detection of serine proteases

| Bottle no. | Reagent | Mol. wt (g/mol) | Reconstitution in | Stock |
|---|---|---|---|---|
| 1 | FP—$N_3$ (2 mg) | 414 | 1 mL DMSO | 4.8 mM |
| 2 | Trypsin (1 mg)/ Chymotrypsin (1 mg) | 23300/ 25000 | 1 mL of 50 mM tris buffer (pH 8.0) | ~42 µM |
| 1 | Alkyne biuret-Fe-TAML (1.6 mg) | 803.5 | 0.1 mL of DI water | 20 mM |
| 2 | THPTA (2 mg) | 434.5 | 0.1 mL of DI water | 50 mM |
| 3 | $CuSO_4 \cdot 5H_2O$ (5 mg) | 250 | 1 mL of DI water | 20 mM |
| 4 | Aminoguanidine•HCl (11 mg) | 110.5 | 1 mL of DI water | 100 mM |
| 5 | Sodium ascorbate (19.8 mg) | 198.1 | 1 mL of DI water | 100 mM |
| 6 | 1X Loading buffer | | | 1X |
| 6 | TMB (12 mg) | 240.3 | 1 mL of 0.1N HCL | 50 mM |
| 7 | 30 wt % $H_2O_2$ (commercial) | 34 | — | 8M |

Procedure for 0.5 mL Reactions:

In a 1 mL eppendorf tube, 12 µL of serine proteases i.e trypsin/chymotrypsin, 484 µL of 50 mM tris buffer pH 8.0 and 4 µL of FP-$N_3$ were added, and mixed together at room temperature for 30 minutes. The reaction mixtures were quickly purified by size-exclusion chromatography using Bio-Spin disposable chromatography column filled with Bio-Gel-P-10 to remove any unreacted FP-$N_3$. 100 µL of the reaction mixture was loaded onto 1 mL of Bio-Gel-P-10 column and centrifuged one time at 500 rpm for 30 sec. 200 µL of this purified FP-$N_3$ labeled protein (1 µM) was added to an eppendorf. To this was added 163 µL of 100 mM phosphate buffer pH 7.4 followed by addition of 4 µL of alkyne tailed biuret-Fe-TAML (20 mM), 3 µL of premixed solution of $CuSO_4$ and THPTA ligand (10 µL of 20 mM $CuSO_4$ and 20 µL of 50 mM THPTA ligand stock) and 10 µL of 100 mM aminoguanidine hydrochloride. The reaction mixture was well mixed with the help of a vortex and degassed by bubbling with $N_2$ gas (to remove $O_2$) followed by addition of 10 µL of freshly prepared sodium ascorbate solution under positive flow of $N_2$. For analysis by gel electrophoresis, 10 µL of the reaction mixture was added to 90 µL of 100 mM pH 7.4 phosphate buffer and 100 µL of 1X SDS loading buffer. This solution was then analysed by SDS-PAGE. The gel electrophoresis was carried out at a constant potential of 100 mV for typically 70 min (until the loading buffer band reaches the bottom of the gel). After completion of gel electrophoresis, the gel was taken out of the electrophoresis gel cassette, washed 4 to 5 times with DI water. The gel was removed from the electrophoresis cassette and treated with a mixture of $H_2O_2$ (100 µL; 80 mM) and TMB (100 µL; 0.5 mM) in 40 mM phosphate buffer pH 7.4 with gentle agitation for 2 minutes. A nice blue coloured band appeared for the serine proteases labeled with FP-Fe-TAML on the gel. The colour of the blue band was further intensified by incubating with 50 mM phosphate buffer pH 4.5.

What is claimed is:

1. A method for in-gel visual detection and quantitative detection of a bioanalyte comprising:
contacting the bioanalyte with a compound of formula (I)

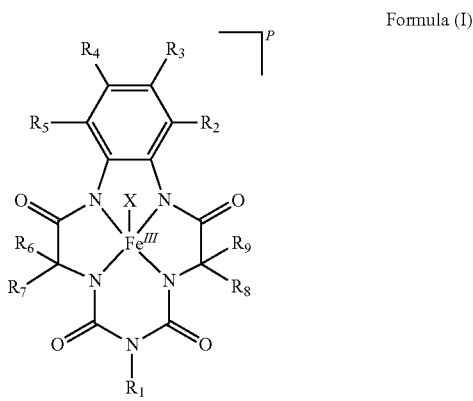

Formula (I)

wherein, X is a mono ionic ligand, selected from chloro, bromo or iodo or is a neutral ligand, and $R_1$, $R_2$, $R_3$, $R_4$, $R_5$, $R_6$, $R_7$, $R_8$ and $R_9$ are the same or are different and are selected form the group consisting of hydrogen, alkyl, alkenyl, alkynyl, aryl, alkoxy, phenoxy, halogen, halogenated alkyl, halogenated alkenyl, halogenated alkynyl, a substituted or unsubstituted cycloalkyl ring, substituted or unsubstituted cycloalkenyl ring, a substituted or unsubstituted saturated heterocyclic ring, a substituted or unsubstituted unsaturated heterocyclic ring, carboxylic acid, carboxylic acid ester, carboxylic acid halides, amines, nitro, and nitrile, and, wherein P is a cation selected from Li, Na, K, $Et_4N$ or $Ph_4P$, wherein the compound of formula (I) is covalently attached to the bioanalyte; and observing a blue colored band for the bioanalyte.

2. The method as claimed in claim 1, wherein said method is conducted by catalytic signal amplification in activity based protein profiling (ABPP).

3. The method as claimed in claim 1, wherein, the compound of formula I is a horseradish peroxidase mimic $Fe^{III}$-TAML complex of a ligand.

4. The method as claimed in claim 1, wherein, the method further comprises:
   a) treating the bioanalyte with an inhibitor probe that has an organoazide handle so as to obtain an azide labelled bioanalyte;
   b) subjecting the azide labelled bioanalyte of step (a) to click reaction with an alkyne-tagged biuret-Fe-TAML, resulting in a click reaction product;
   c) running the click reaction product of step (b) on a polyacrylamide gel followed by probing with $H_2O_2$ and 3,3',5,5'-Tetramethylbenzidine.

5. The method as claimed in claim 4, wherein, the organoazide is maleimide-azide.

6. The method as claimed in claim 4, wherein, the bioanalyte is selected from the group proteins, enzymes, antibodies, or nucleic acids.

7. A gel comprising the compound of formula (I) and a bioanalyte

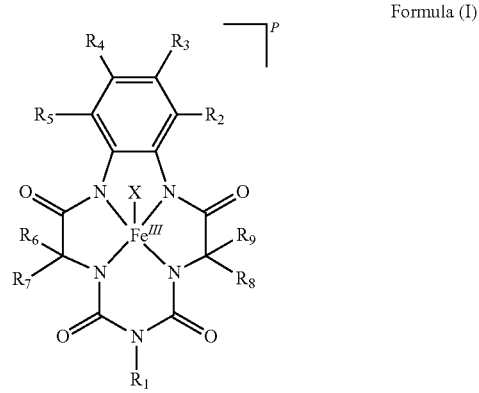

Formula (I)

wherein, X is a mono ionic ligand, selected from chloro, bromo or iodo or is a neutral ligand and $R_1$, $R_2$, $R_3$, $R_4$, $R_5$, $R_6$, $R_7$, $R_8$ and $R_9$ are the same or are different and are selected form the group consisting of hydrogen, alkyl, alkenyl, alkynyl, aryl, alkoxy, phenoxy, halogen, halogenated alkyl, halogenated alkenyl, halogenated alkynyl, a substituted or unsubstituted cycloalkyl ring, substituted or unsubstituted cycloalkenyl ring, a substituted or unsubstituted saturated heterocyclic ring, a substituted or unsubstituted unsaturated heterocyclic ring, carboxylic acid, carboxylic acid ester, carboxylic acid halides, amines, nitro, and nitrile and wherein, P is a cation selected from Li, Na, K, $Et_4N$ or $Ph_4P$; and wherein, the compound of formula (I) is covalently attached to the bioanalyte.

8. The gel as claimed in claim 7, wherein, the compound is biuret-Fe-TAML complex.

9. The gel as claimed in claim 7, wherein, the gel is a polyacrylamide gel.

10. The gel as claimed in claim 8, wherein, the gel is a polyacrylamide gel.

11. The gel as claimed in claim 7, wherein, the bioanalyte is selected from proteins, enzymes, antibodies, or nucleic acids.

12. The gel as claimed in claim 8, wherein, the bioanalyte is selected from proteins, enzymes, antibodies, or nucleic acids.

13. The gel as claimed in claim 7, wherein, the gel further comprises a probe activating compound.

14. The gel as claimed in claim 13, wherein, the probe activating compound is $H_2O_2$ or TMB or a combination thereof.

15. The gel as claimed in claim 8, wherein, the gel further comprises a probe activating compound.

16. The gel as claimed in claim 15, wherein, the probe activating compound is $H_2O_2$ or TMB or a combination thereof.

* * * * *